United States Patent [19]

Fitzpatrick

[11] Patent Number: 4,625,167

[45] Date of Patent: Nov. 25, 1986

[54] FLAW IMAGING IN FERROUS AND NONFERROUS MATERIALS USING MAGNETO-OPTIC VISUALIZATION

[75] Inventor: Gerald L. Fitzpatrick, Issaquah, Wash.

[73] Assignee: Sigma Research, Inc., Richland, Wash.

[21] Appl. No.: 510,662

[22] Filed: Jul. 5, 1983

[51] Int. Cl.[4] .................... G01N 27/82; G01N 21/21; G02F 1/09
[52] U.S. Cl. .................................. 324/235; 324/213; 324/238; 350/377; 356/237
[58] Field of Search ................ 324/200, 228, 213–216, 324/244, 262, 96, 235, 238; 350/374–378; 250/225; 356/237

[56] References Cited

U.S. PATENT DOCUMENTS

| | | | |
|---|---|---|---|
| 3,443,214 | 5/1969 | Meservey | 324/214 |
| 3,564,924 | 2/1971 | De Sorbo | 324/244 X |
| 3,594,064 | 7/1971 | Bierlein | 350/377 X |
| 3,650,601 | 3/1972 | Bierlein | 350/377 X |
| 3,893,023 | 7/1975 | Otala | 324/244 |
| 4,064,453 | 12/1977 | Haas et al. | 324/244 X |

FOREIGN PATENT DOCUMENTS

| | | | |
|---|---|---|---|
| 0058461 | 4/1983 | Japan | 324/214 |
| 0697905 | 11/1979 | U.S.S.R. | 324/216 |

*Primary Examiner*—Gerard R. Strecker
*Attorney, Agent, or Firm*—Blakely, Sokoloff, Taylor & Zafman

[57] ABSTRACT

A method for the direct visualization of surface and near surface cracks, voids, flaws, discontinuities, etc. in materials is disclosed. The detection of flaws or the like is accomplished by the visualization of the static and/or dynamic magnetic fields, either ambient or induced, associated with various flaws in a target material. A magnetic garnet epitaxial film is deposited on a non-magnetic substrate. In one embodiment, a reflective coating or material is provided adjacent to the epitaxial film, and the substrate with its associated layers is placed over the target material. A magnetic field is then applied to the target material and substrate. Polarized light is directed onto the through the substrate and associated epitaxial layer, and is reflected by the reflective coating such that the polarized light passes back out of the substrate. The existing magnetization within the epitaxial film interacts with nearby magnetic fields associated with near surface flaws in the target material, such that the domain structure of the epitaxial film is altered. The altered domain structure induces a rotation of the plane of polarization of the incident projected light. When viewed through a polarizing material, the rotation of the reflected light renders the magnetic field variations associated with the flaws directly visible. Accordingly, surface and near surface flaws are optically detected. An alternate embodiment is disclosed which utilizes a transmission geometry.

17 Claims, 7 Drawing Figures

FLAW IMAGING IN FERROUS AND NONFERROUS MATERIALS USING MAGNETO-OPTIC VISUALIZATION

BACKGROUND OF THE INVENTION

1. Field

The present invention relates to the field of detecting flaws and discontinuities in materials, and more particularly, to the detection of flaws and discontinuities in materials using magneto-optic visualization.

2. Art Background

In many scientific, engineering and manufacturing applications, near surface cracks, voids, discontinuities and flaws in ferrous or nonferrous materials must be detected in order to insure the structural integrity of a material. For example, the material integrity of components comprising many air and space vehicles is critical for their proper operation, especially with regard to high stress components such as turbine and fan blades, rocket engine systems, air frames, etc.

A number of techniques have been developed and utilized in order to detect cracks, flaws or the like in materials. For example, magnetic particle methods have been employed which utilize static or "low" frequency (less than 100 Hz) magnetic fields having field components parallel to the surface of ferrous alloys which are induced by currents paralleling these surfaces. The parallel surface currents in turn may be induced, either directly by contact electrodes, or indirectly using coils surrounding the target material and low frequency excitation. Magnetic fields paralleling the surfaces of the target material are distorted by cracks or near surface flaws and these distortions may be detected through the use of a magnetic powder deposited on the material. Various types of magnetic powders have been developed for the visualization of sub-surface flaws. Each magnetic particle in these powders typically consists of a single magnetic domain (i.e. a region of essentially uniform magnetization). When the magnetic powder is applied dry or in a wet slurry to a target material where a crack or flaw is present, the magnetic particles tend to aggregate and form a bridge in regions of field non-uniformities which are associated with the flaw. By mixing various pigments, fluorescent dyes, and the like, with the magnetic powder, the cracks or flaws are rendered visible.

Although the magnetic powder technique is widely employed, it is a dirty, and time consuming method which requires the induction of large surface currents in the material under study. Magnetic particle methods are best suited for use with low frequencies and ferrous alloys. The large masses of magnetic particles required renders the magnetic powder techniques ineffective when high frequencies are used.

Another method which has been utilized in order to detect flaws or cracks in materials is the "eddy" current technique. Eddy current techniques typically utilize a time varying electromagnetic field which is applied to the target material being examined. Non-contact coils may then be used to excite eddy currents in the target material, such that these currents tend to flow around flaws and result in field distortions which allow the flaw to be detected in a number of well known ways. For example, circuit parameters characterizing the mutual interaction between the exciting coil and the responding material may comprise the parameters of capacitance, inductance or reactance. However, eddy current techniques require a considerable amount of support equipment and most techniques do not result in a flaw image but rather produce data from which flaw information can be obtained only after appropriate analysis has been completed.

As will be described, the present invention provides a method for the direct optical visualization of surface and near surface cracks, flaws, etc. in ferrous and nonferrous materials. The present invention provides direct visualization of both the static and/or dynamic magnetic fields associated with the various flaws or other discontinuities in a target material, and overcomes the disadvantages associated with prior art material flaw imaging methods. In addition, the present invention is compatible with the requirements of eddy current methods while producing images of flaws directly, without the additional support equipment and data analysis required by most eddy current systems.

SUMMARY OF THE INVENTION

A method for the direct visualization of surface and near surface cracks, voids, flaws, discontinuities, etc. in a material is disclosed. The detection of flaws or the like is accomplished by the visualization of the static and/or dynamic magnetic fields, either ambient or induced, associated with various flaws in a target material.

A magnetic garnet epitaxial film is deposited on a non-magnetic substrate. In one embodiment, a reflective coating or material is provided adjacent to the epitaxial film, and the substrate with its associated layers is placed over the target material. A magnetic field is then applied to the target material and substrate. Polarized light is directed onto and through the substrate and associated expitaxial layer, and is reflected by the reflective coating such that the polarized light again passes through the epitaxial layer and back out of the substrate. The existing magnetization within the epitaxial film interacts with nearby magnetic fields associated with near surface flaws in the target material, such that the domain structure of the epitaxial film is altered. The altered domain structure induces a rotation of the plane of polarization of the incident projected light. When viewed through a polarizing material, the rotation of the reflected light renders the magnetic field variations associated with the flaws directly visible. Accordingly, surface and near surface flaws are optically detected. An alternate embodiment is disclosed which utilizes a transmission geometry.

DETAILED DESCRIPTION OF THE INVENTION

A method for magneto-optically visualizing flaws, inclusions, voids, discontinuities, etc. (hereinafter collectively referred to as "flaws") in ferrous and nonferrous materials is disclosed. In the following description for purposes of explanation, numerous details are set forth such as specific garnet materials, substrates, optical configurations, magnetic fields, currents, frequencies, etc. in order to provide a thorough understanding of the present invention. However, it will be apparent to one skilled in the art that the invention may be practiced without these specific details. In other instances, well known optical components, structures and electrical processing means have not been described in detail in order not to obscure the present invention unnecessarily.

Figure 1:
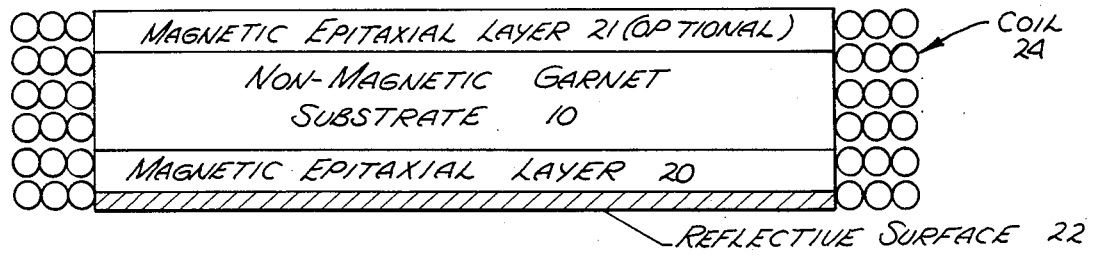
FIG. 1 illustrates an epitaxial garnet film and reflective coating disposed on a non-magnetic substrate.

Referring now to FIG. 1, the presently preferred embodiment of the invention utilizes a non-magnetic garnet substrate 10 on which magnetic garnet epitaxial layer 20 and an optional layer 21 is disposed. As shown, a reflective surface 22 is provided using well known depostion techniques or materials on the epitaxial layer 20, such that incident light passing through the substrate 10 and layers 20 and 21 is reflected back through layer 20, substrate 10 and layer 21, and flaws thereby imaged in a manner which will be discussed more fully below. It will be noted that the reflective surface 22 may comprise a front surface mirror or "scotchlite" type coating (which is a retroreflective coating) as well as other numerous deposited reflective coatings. As shown in FIG. 1, an electrical coil 24 is disposed around substrate 10 with its associated layers. As will be discussed, coil 24 is provided with an electric potential in order to induce a current I in the coil which produces a magnetic field through both substrate 10 and magnetic layers 20 and 21 as well as a target material which is to be tested for flaws or other discontinuities. For purposes of this Specification, the term "epitaxial layer" or "epitaxial garnet layer" is understood to mean any one of a variety of suitable magneto-optically active film types having magneto-optic activity as required by the present invention for any particular application.

Figure 2A:
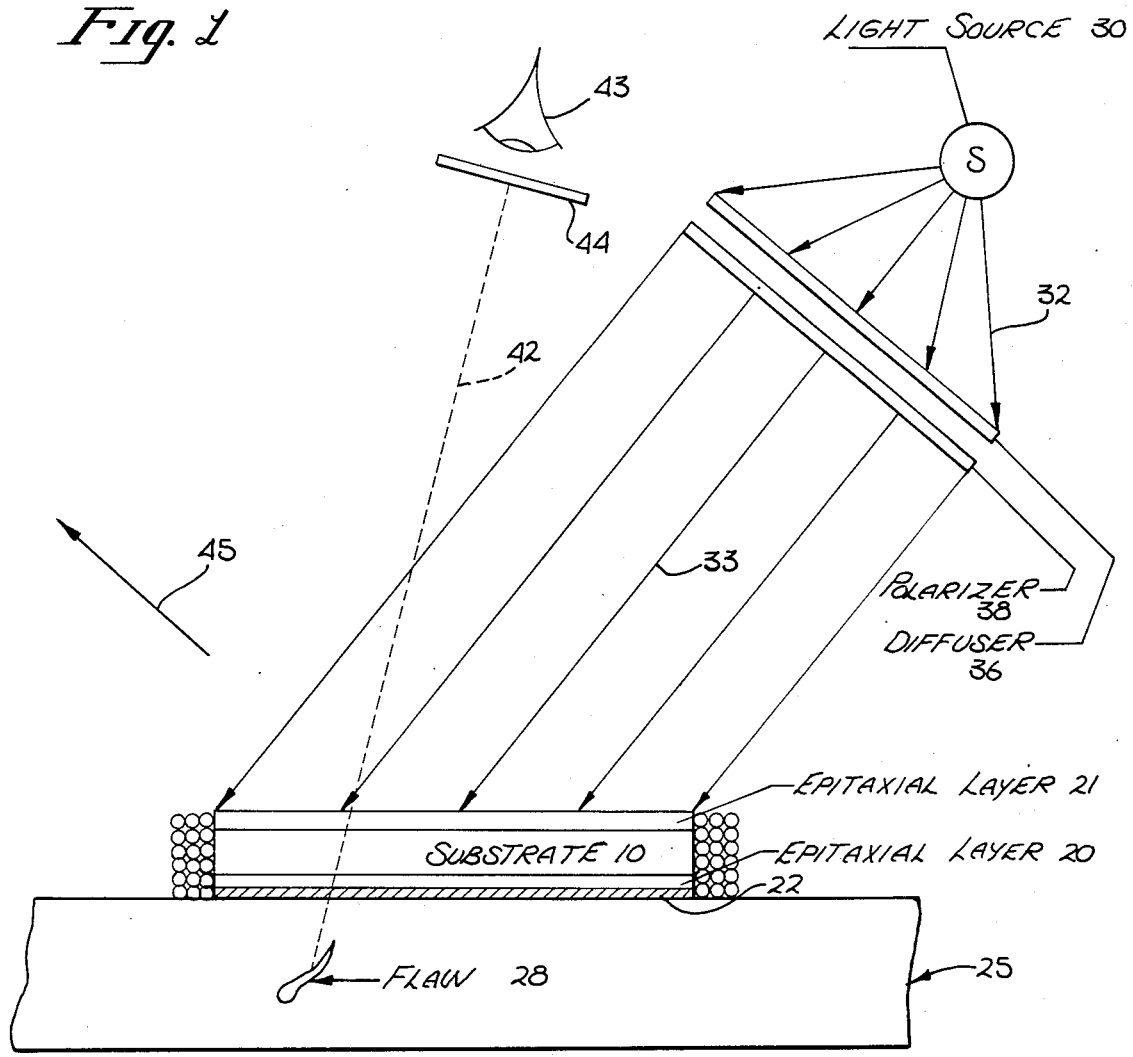
FIG. 2(a) illustrates one embodiment of the present invention utilizing a reflection geometry to optically detect flaws within a test material.

With reference now to FIG. 2(a), one embodiment of the present invention is disclosed which utilizes a reflection geometry. A target material 25 is provided which may include an unknown flaw 28 within the structure of the material 25. Substrate 10 with its magnetic epitaxial layers 20 and 21 is disposed over a portion of the target material 25 to be examined. A magnetic field is applied to the test material 25 and substrate 10 with its applied layers 20, 21 and 22 by passing a current through coil 24 or, alternatively, by attaching electrodes to the material. A light source 30 which may comprise, for example, an incandescent bulb, single wave-length laser, fluorescent lamp, or the like is provided in order to generate incident light beams 32. A diffuser 36 is provided to diffuse light rays 32 generated by light source 30. Similarly, a polarizer 38 is disposed adjacent to and in optical alignment with the diffuser 36 such that light generated by light source 30 is linearly polarized after passing through diffuser 36. As shown in FIG. 2(a), the now polarized light 33 is projected onto the substrate 10 with associated layers disposed above the target material 25, and, as will be discussed more fully below, flaws 28 are rendered directly visible by observing the reflected radiation 42 reflected off of reflective surface 22 and passing through a second polarizer 44. As shown, unwanted surface reflections 45 are reflected off of layer 21 and away from the second polarizer 44.

When the polarized light 33 is incident on the magnetic garnet epitaxial layer 20, the plane of polarization of the incident light will be rotated by an angle which may be described by the following relationship:

$$\theta \alpha \theta_f \overline{K} \cdot \overline{M}$$

where $\theta_f$ is the specific Faraday rotation of the layer 20, $\overline{K}$ is the wavevector of the incident light, and the $\overline{M}$ is the local magnetization of the epitaxial layer 20 at the point where the incident light passes through the layer. The sign of the scalar product $\overline{K} \cdot \overline{M}$ determines the sense of the rotation. It will be noted that in the case of a solid, the Faraday rotation does not depend on the sign of the wavevector $\overline{K}$, but only on the angle between $\overline{K}$ and $\overline{M}$. Thus, the effect of rotation is doubled by the reflective surface 22 disposed between the upper surface of the target material 25 and the magnetic garnet epitaxial layer 20. The reflective surface 22 ensures that the incident light 33 will pass back through the epitaxial layer 20 and thereby double the effective rotation of the plane of polarization. It will be appreciated that although not required, the presently preferred embodiment includes second epitaxial layer 21 disposed above substrate 10. This second layer 21 is generally separated from lower layer 20 by approximately 0.02 inches (the thickness of substrate 10), and has been found to increase the sensitivity of the present invention and improve contrast. However, for purposes of clarity, the analysis of the operation of the present invention disclosed hereinbelow will assume layer 21 is not present.

The difference in the rotation of the plane of polarization of the incident linearly polarized light 33 and the reflected light 42 which passes through the epitaxial layer 20 permits the direct visualization of flaws within material 25. In addition, it has been found that the present invention also permits the visualization of the existing state of magnetization in materials 25 due to prior magnetic history or present conditions such as electromagnetic fields, stress fields, or temperature gradients. Ordinarily, in the absence of an applied magnetic field, magnetic domains (regions of uniform magnetization in the epitaxial layer 20) are relatively small. In many epitaxial magnetic garnet films, especially those used in magnetic bubble memories or the like, domains typically measure several microns across. In other epitaxial films, small applied fields (of for example 100 Gauss or less) can cause the magnetic domains to coalesce into large domains several centimeters across in epitaxial layers having only slightly larger dimensions.

Figure 3:
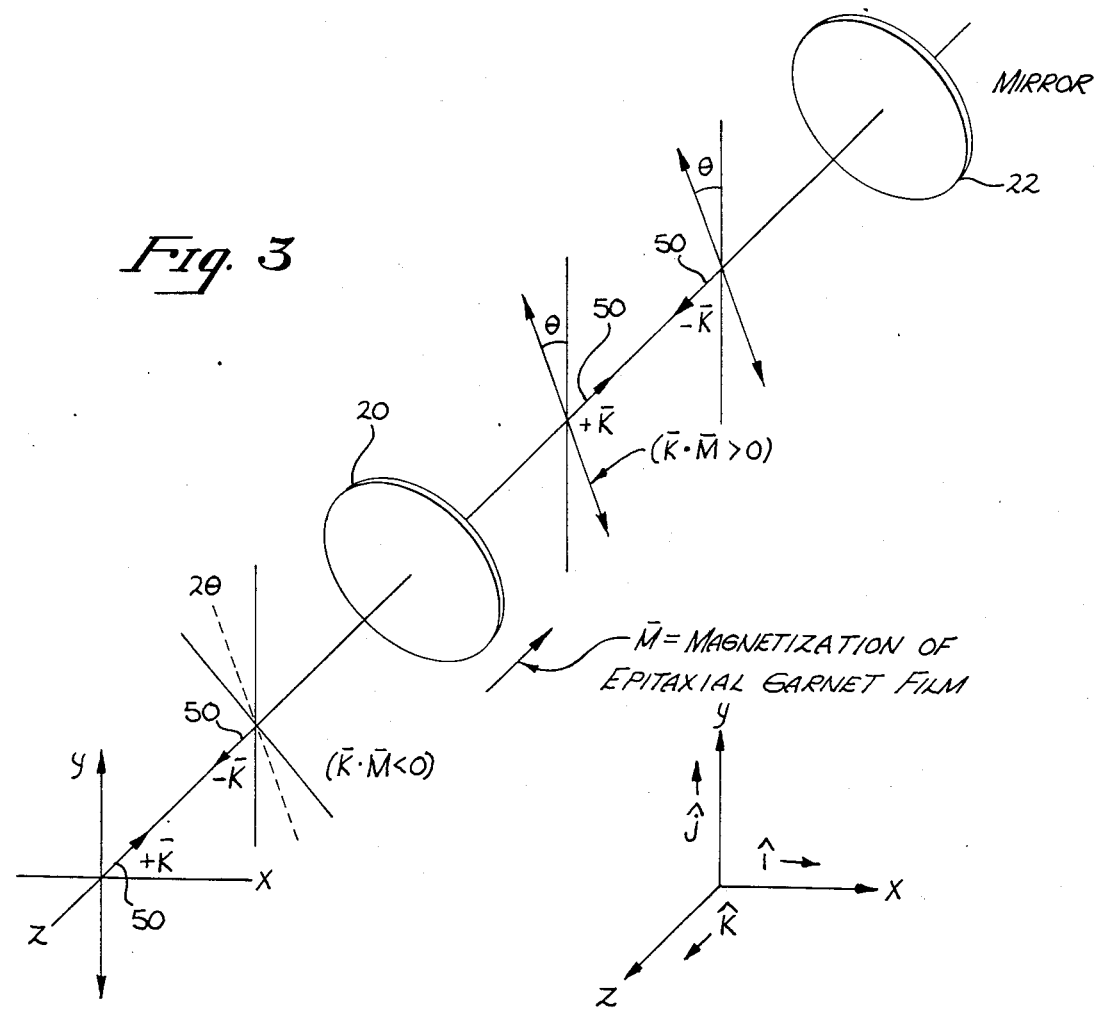
FIG. 3 illustrates the Faraday effect of a magneto-optically active garnet film on the plane of polarization of an incident light wave.

Referring now to FIG. 3, the effect of a magnetic garnet epitaxial layer 20 on the plane of polarization of incident light 33 is illustrated. A light wave 50 which is one representative ray of incident light 33 has a wave vector $+\overline{K}$ along the negative Z axis which is linearly polarized along the Y axis. As light wave 50 passes through epitaxial layer 20 travelling toward surface 22, the polarization of light wave 50 is rotated counter-clock-wise by an angle $\theta$. As light wave 50 impinges on reflective surface 22, the wave vector is reversed and light wave 50 again passes through the epitaxial layer 20. Thus, a doubled Faraday rotation of the polarization of wave 50 occurs such that the plane of polarization of the light wave 50 is now $2\theta$ with reference to the Y axis of original polarization direction.

Figure 4A:
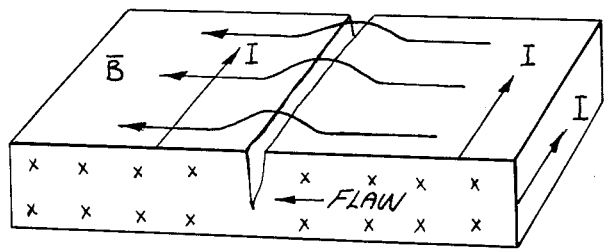
FIG. 4(a) illustrates magnetic fields induced by currents which effectively "jump" a flaw or other discontinuity in a test material.
Figure 4B:
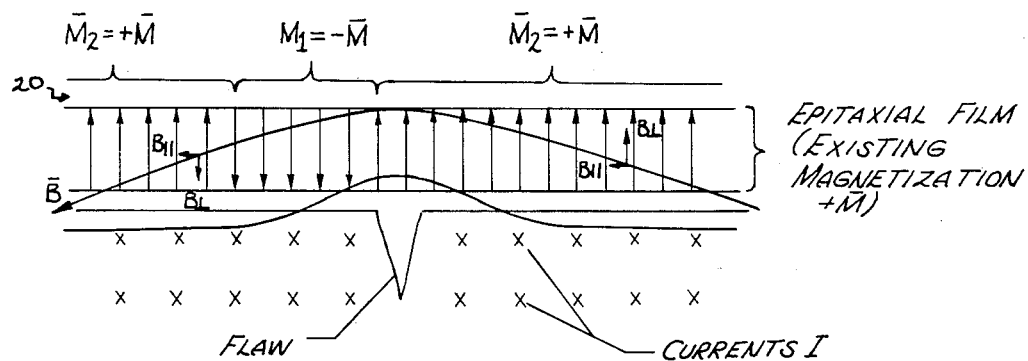
FIG. 4(b) illustrates the domain structure of the epitaxial layer in the presence of a magnetic field.
Figure 4C:
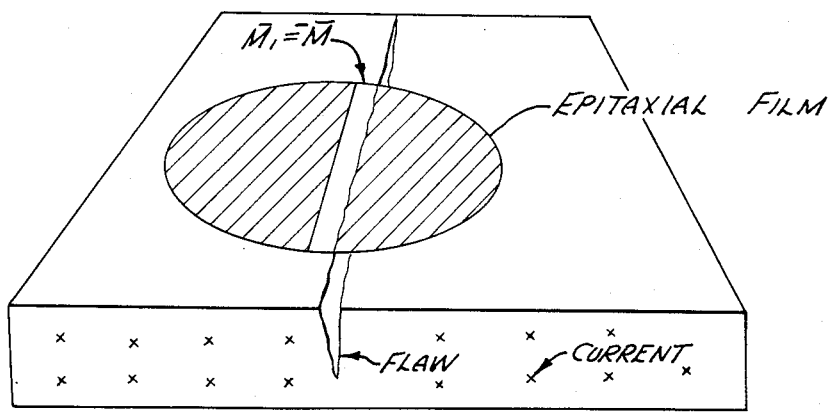
FIG. 4(c) illustrates an image magneto-optically produced of a flaw within a test material using the teachings of the present invention.

Referring now to FIGS. 4(a)–(c), it will be appreciated that the magnetic fields associated with a flaw are capable of switching the direction of existing magnetization at some point in the epitaxial layer 20 from $+\overline{M}$ to $-\overline{M}$. As shown in FIG. 4(a), a small flaw 28 has an associated magnetic field ("B field") distortion which will switch the magnetization of epitaxial layer 20 in regions parallel to the flaw (see FIG. 4(b)). The plane of polarization of the light which passes through the region with magnetization $\overline{M}_1 = -\overline{M}$ is rotated by an angle $\theta\alpha\overline{K}_1\cdot\overline{M}_1 > 0$ but the plane of polarization of the light that passes through the adjacent region with magnetization $\overline{M}_2 = +\overline{M}$ is rotated by an angle $\theta\alpha\overline{F}_1\cdot\overline{M}_2 < 0 |\theta_1| \simeq |\theta_2| \simeq \theta$). Thus, the total angle between the planes of polarization of the two light waves initially is zero, whereas after passing through the two adjacent regions having opposite magnetization it is:

$$2\theta \simeq |\theta_1| + |\theta_2|$$

As indicated in FIG. 3, the effect of reflective surface 22 is to double the angle of rotation of polarization, resulting in an angle of $4\theta$ between the planes of polarization of the two light waves upon passage back through the epitaxial layer 20. The light 42 which is returned to the viewer 43 is passed through a second polarizer 44 (referred to as an "analyzer"), and the flaw or other subsurface detect is thereby detected. In practice this is accomplished by setting the analyzer 44 to block one and pass the other of two light waves, the planes of polarization of which are separated by an angle of $4\theta$ when two epitaxial layers 20 and 21 are used. Thus two adjacent regions having reversed magnetization $\overline{M}_1$ and $\overline{M}_2$ in each of the two epitaxial layers 20 and 21 are seen as being dark (light) or light (dark) respectively, depending on the setting of the analyzer 44. In other words, the region of "reversed" magnetization adjacent to the flaw boundary is rendered visible as illustrated in FIG. 4(c).

Thus, the present invention images perturbations of the state of existing magnetization in a particular region of the epitaxial layer 20 by either changing the magnitude and direction of the existing magnetization or reversing (switching) the magnetization in the region of layer 20 above the flaw in material 25 altogether. These perturbations are then visually "imaged" by the returned polarized light 42 through the use of polarizing analyzer 44. The addition of optional layer 21 does not alter the operation of the present invention but rather further doubles the rotation of the plane of polarization of the incident light 33.

Figure 2B:
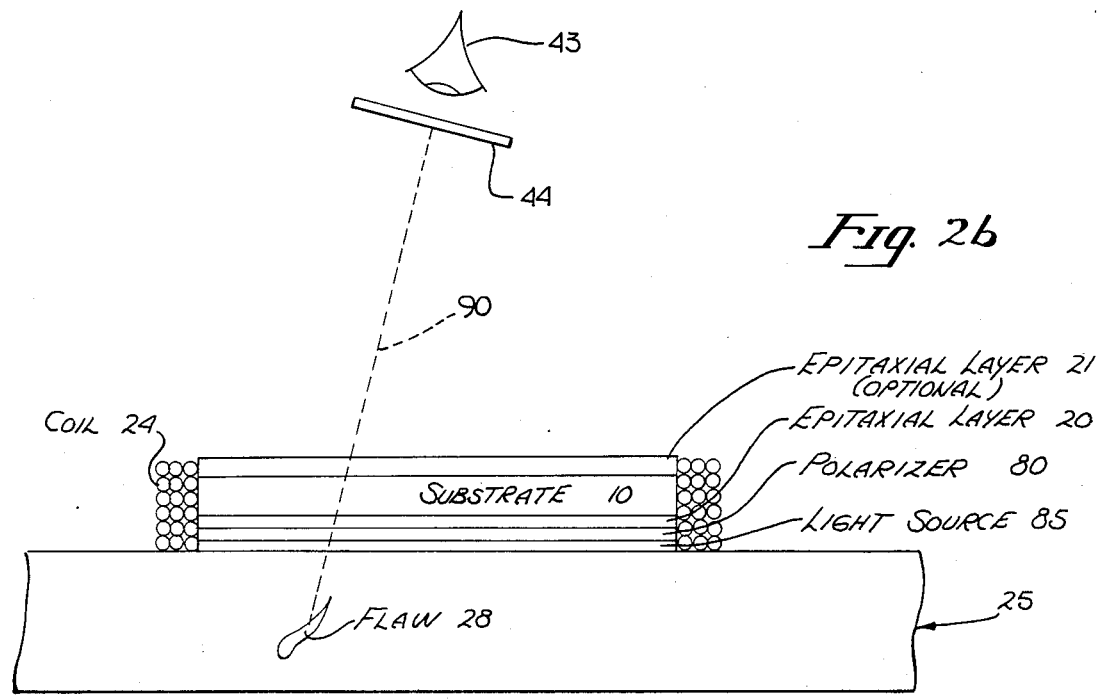
FIG. 2(b) illustrates another embodiment of the present invention utilizing a transmission geometry in order to optically detect flaws within a test material.

Referring briefly to FIG. 2(b), an alternate embodiment of the present invention is disclosed wherein a transmission geometry is utilized. As in the embodiment illustration in FIG. 2(a), a non-magnetic substrate 10 is provided on which magnetic garnet epitaxial layers 20 and 21 are disposed. A linear polarizer 80 is sandwiched between the epitaxial layer 20 and a diffuse light source 85, such as an electroluminescent panel coupled to a voltage source. As shown, the substrate 10, magnetic epitaxial layers 20 and 21, polarizer 80, and the diffuse light source 85 is sourrounded by coil 24 and forms an assembly which is placed in contact with material 25 to be tested having a flaw 28. The diffuse light source 85 generates light which passes upwardly through polarizing layer 80, layer 20, substrate 10, and through epitaxial layer 21. By viewing the light 90 passing through the epitaxial layers 20 and 21, through polarizer 44, magnetic field reversals and other magnetic field perturbations caused by flaw 28 in epitaxial layer 20 may be directly viewed. Thus, the theory of operation of the embodiment disclosed in FIG. 2(b) is substantially the same as that described with reference to FIG. 2(a). Accordingly, just as in the case of FIG. 2(a), flaws are rendered visible as a result of the rotation of the plane of polarization of incident light passing through layer 20 and optional layer 21.

The foregoing disclosure related to the present invention assumed frequencies being substantially zero. It will be apparent to one skilled in the art, that if the magnetic fields are reversed, due to current reversals or the like, (i.e. AC signals), these fields are capable of switching the magnetization of the epitaxial layer 20 from $+\overline{M}$ to $-\overline{M}$. In such an event, the pattern of light and dark as seen through the polarizing analyzer 44 is in synchrony with these current reversals. If an alternating field is present as is the case of the eddy current methods known in the prior art, it will be apparent that the image viewed through the analyzer 44 would tend to average to some uniform value and therefore "washout" the flaw image. There are a number of methods which may be used in order to preserve the flaw image in the case of current reversals. One solution is to amplitude modulate the illumination of the epitaxial layer 20 at the same frequency and in some fixed phase relation with the current reversals. Similarly, it is possible to amplitude modulate the induced currents in the test material 25. Moreover, for very low frequency applications it is possible to "chop" the incident light wave 33 of FIG. 2(a) in synchrony with the applied magnetic fields. For higher frequency applications the incident light 33 could be amplitude modulated with various devices.

By amplitude modulating the incident light 33 in this or some other manner, dark areas of a scene would always be viewed by a detector or the eye through analyzer 44 as dark, and light areas of the scene would always appear light. Thus, the flaw 28 could be directly viewed even in the situation where the fields vary in time (e.x. the eddy current case). By adjusting the frequency of the electromagnetic field which excites the eddy currents, one can control the skin depth (the depth of penetration of the exitation wave), and therefore obtain information relative to the depth of the flaws detected by the present invention's method.

Pulsed direct currents or amplitude modulated electromagnetic fields, which excite essentially pulsed direct currents in the test material 25 may also be emloyed in order to utilize the present invention where the fields are varying in time. Accordingly, when viewing a scene through the analyzer 44, the magnetization directions in the epitaxial layer under conditions of constant light intensity would tend to maintain their direction and thus the image of flaws within the material 25 would be rendered visible and not washed out as in the case of time varying currents and fields.

Accordingly, a method and apparatus for the direct visualization of surface and near surface cracks, flaws, etc. in materials has been disclosed. The invention provides a simple and economical means for detecting flaws not possible in the prior art. It will be understood that various changes may be made in the details, arrangements and proportions of the various elements of the present invention without departing from the spirit and scope of the invention. For example, it will be apparent that the present invention has utility beyond the detection of flaws in non-organic materials and may be used to detect tumors or other discontinuities in biologic materials.

I claim:

1. An apparatus for detecting and providing images of flaws, voids, discontinuities, or the like in a target material, comprising:
    a magnetic material having a plurality of magnetic domains, said magnetic material comprising a first magnetic epitaxial layer disposed on a first surface of a non-magnetic substrate and a second magnetic epitaxial layer disposed on a second surface of said non-magnetic substrate, said first magnetic epitaxial layer being placed in proximity to said target material;
    magnetic field generation means disposed about said magnetic material for generating and applying a variable magnetic field to said target material and to said magnetic material;
    light gneration means disposed above said second magnetic epitaxial layer for generating polarized light and projecting said polarized light through said magnetic material and onto said target material, said projected light reflecting from said target material and through said magnetic material;
    analyzer means disposed above said second magnetic epitaxial layer and away from said light generation means for observing the rotation of the plane of polarization of said reflected light;
    said polarization plane being rotated as a result of the realignment of said magnetic domains caused by magnetic field perturbations in areas of said magnetic material in proximity to a flaw, void, discontinuity or the like, in said target material;
    whereby an image of said flaw, void, discontinuity or the like is detected by observing magnetic field perturbations in said magnetic material.

2. The apparatus as defined by claim 1 wherein said magnetic field perturbations alter the distribution of said magnetic domains in said magnetic material.

3. The apparatus as defined by claim 2 wherein said first and second magnetic epitaxial layers comprise a magnetic epitaxial garnet layer.

4. The apparatus as defined by claim 3 wherein said light generation means includes a light source with a polarizing material disposed in optical alignment with said magnetic material.

5. The apparatus as defined by claim 4 further including a reflective coating disposed on said first epitaxial layer such that said incident polarized light is reflected back through and out of said substrate.

6. The apparatus as defined by claim 4 wherein the rotation of the plane of polarization of the incident light on each of said magnetic epitaxial layers is described by the following relationship:

$$\theta \alpha \theta_f \overline{K} \cdot \overline{M}$$

where
    $\theta_f$ = the specific Faraday rotation of each of said magnetic epitaxial layers,
    $\overline{K}$ = the wavevector of the incident polarized light,
    $\overline{M}$ = the local magnetization of each of said magnetic epitaxial layers.

7. The apparatus as defined by claim 6 wherein said magnetic field perturbations constitute field reversals in proximity to a boundary of a flaw, void or like in said target material.

8. The apparatus as defined by claim 6 wherein said magnetic field perturbations constitute changes in the size and direction of the existing magnetic domains which are in proximity to a boundary of a flaw, void or the like in said target material whereby an image of said flaw, void or the like is formed in said magnetic material.

9. The apparatus as defined by claim 6 wherein said magnetic field generation means generates an alternating (AC) magnetic field; and said incident polarized light is modulated in synchrony with said magnetic field such that the output of said analyzer remains substantially constant.

10. The apparatus as defined by claim 6 wherein said magnetic field generation means is coupled to an alternating current (AC) source and a direct current (DC) source for stimulating said magnetic field generation means to generate an alternating magnetic field of a first frequency;
    said target materials coupled to an alternating current source such that a magnetic field is applied to said target at a second frequency;
    whereby an image is produced in said magnetic material which varies at the frequency difference between said first and second frequency.

11. The apparatus as defined by claim 9 further including a retroreflective coating disposed on said first epitaxial layer such that said incident polarized light is reflected back through and out of said substrate.

12. A method for detecting and providing images of flaws, voids, discontinuities and the like in a target material, comprising the steps of:
    placing a magnetic material having a first magnetic epitaxial layer disposed on a first surface of a non-magnetic substrate and a second magnetic epitaxial layer disposed on a second surface of said non-magnetic substrate in proximity to said target material;
    applying a variable magnetic field to said target material and said magnetic material;
    projecting polarized light from a source disposed above said magnetic material through said magnetic material onto said target material, said polarized light reflecting from said target material and through said magnetic material;
    observing the rotation of the plane of polarization of said reflected light;
    said polarization plane being rotated as a result of the realignment of said magentic domains caused by magnetic field perturbations in said areas of said magnetic material in proximity to a flaw, void, discontinuity or the like in said target material;
    whereby said flaw, void, discontinuity or the like is detected and imaged by observing magnetic field perturbations in said magnetic material.

13. The method as defined by claim 12 wherein said magnetic field perturbations alter the distribution of said magnetic domains in said magnetic material.

14. The method as defined by claim 13 wherein said first and second magnetic epitaxial layers comprise a magnetic iron garnet epitaxial layer.

15. The method as defined by claim 14 further including the step of depositing a reflective coating onto said epitaxial layer such that said incident polarized light passes through said epitaxial layer and is reflected back through and out of said epitaxial layer and substrate.

16. The method as defined by claim 14 wherein the rotation of the plane of polarization of the incident light on each of said first and second magnetic epitaxial layers is described by the following relationship:

$$\theta \alpha \theta_f \overline{K} \cdot \overline{M}$$

where,
$\theta_f$ = the specific Faraday rotation of each of said magnetic epitaxial layers,
$\overline{K}$ = the wavevector of the incident polarized light,
$\overline{M}$ = the local magnetization of each of said magnetic epitaxial layers.

17. The method as defined by claim 16 further including the step of depositing a retroreflective coating onto said first epitaxial layer such that said incident polarized light passing through said epitaxial layer is reflected back through and out of said epitaxial layer and substrate.

* * * * *